(12) United States Patent
Yamaguchi

(10) Patent No.: US 11,443,463 B2
(45) Date of Patent: Sep. 13, 2022

(54) X-RAY CT APPARATUS, IMAGE RECONSTRUCTION DEVICE, AND IMAGE RECONSTRUCTION METHOD

(71) Applicant: SUMITOMO HEAVY INDUSTRIES, LTD., Tokyo (JP)

(72) Inventor: Takashi Yamaguchi, Kanagawa (JP)

(73) Assignee: SUMITOMO HEAVY INDUSTRIES, LTD., Tokyo (JP)

(*) Notice: Subject to any disclaimer, the term of this patent is extended or adjusted under 35 U.S.C. 154(b) by 129 days.

(21) Appl. No.: 16/818,636

(22) Filed: Mar. 13, 2020

(65) Prior Publication Data

US 2020/0294281 A1    Sep. 17, 2020

(30) Foreign Application Priority Data

Mar. 15, 2019    (JP) .............................. JP2019-048696

(51) Int. Cl.
*G06T 11/00* (2006.01)
*A61B 6/00* (2006.01)
*A61B 6/03* (2006.01)

(52) U.S. Cl.
CPC ............ *G06T 11/005* (2013.01); *A61B 6/032* (2013.01); *A61B 6/5282* (2013.01); *G06T 2210/41* (2013.01)

(58) Field of Classification Search
CPC ... G06T 11/005; G06T 2210/41; A61B 6/032; A61B 6/5282; A61B 6/5205; A61B 6/5211; A61N 2005/1061; A61N 2005/1087
See application file for complete search history.

(56) References Cited

U.S. PATENT DOCUMENTS

| 10,143,436 B2 | 12/2018 | Nishimura et al. | |
| 2017/0116717 A1* | 4/2017 | Naito | G06T 7/0012 |
| 2018/0268573 A1* | 9/2018 | Fukuda | A61B 6/5282 |

FOREIGN PATENT DOCUMENTS

JP    2014-124206 A    7/2014

* cited by examiner

*Primary Examiner* — Courtney D Thomas
(74) *Attorney, Agent, or Firm* — Michael Best & Friedrich LLP

(57) ABSTRACT

Provided is an X-ray CT apparatus including an X-ray irradiation unit that rotates around a placement portion on which an irradiation target is placed and emits X-rays; an X-ray detection unit that detects the X-rays emitted from the X-ray irradiation unit and passed through the irradiation target; and an image reconstruction unit that reconstructs a tomographic image of the irradiation target based on image data of the X-rays detected by the X-ray detection unit, in which the image reconstruction unit calculates a scattered ray component scattered in each of a plurality of three-dimensional spaces obtained by partitioning the irradiation target by a predetermined size among the X-rays detected by the X-ray detection unit in consideration of an atom number density per unit volume in each of sections included in the plurality of three-dimensional spaces and an atomic number, and reconstructs the tomographic image in consideration of the scattered ray component.

11 Claims, 6 Drawing Sheets

X-RAY CT APPARATUS, IMAGE RECONSTRUCTION DEVICE, AND IMAGE RECONSTRUCTION METHOD

RELATED APPLICATIONS

The content of Japanese Patent Application No. 2019-048696, on the basis of which priority benefits are claimed in an accompanying application data sheet, is in its entirety incorporated here by reference.

BACKGROUND

Technical Field

A certain embodiment of the present invention relates to an X-ray CT apparatus, an image reconstruction device, and an image reconstruction method.

Description of Related Art

In the related art, as a charged particle beam therapy apparatus equipped with an X-ray CT apparatus for performing a reconstruction of a tomographic image of an irradiation target, an apparatus disclosed in the related art is known. The X-ray CT apparatus irradiates an irradiation target with X-rays and acquires X-ray image data based on X-rays passed through the irradiation target, by an X-ray detection unit. Further, the X-ray CT apparatus performs an image reconstruction based on the detected X-ray image data.

SUMMARY

According to an embodiment of the present invention, there is provided an X-ray CT apparatus including: an X-ray irradiation unit that rotates around a placement portion on which an irradiation target is placed and emits X-rays; an X-ray detection unit that detects the X-rays emitted from the X-ray irradiation unit and passed through the irradiation target; and an image reconstruction unit that reconstructs a tomographic image of the irradiation target based on image data of the X-rays detected by the X-ray detection unit, in which the image reconstruction unit calculates a scattered ray component scattered in each of a plurality of three-dimensional spaces obtained by partitioning the irradiation target by a predetermined size among the X-rays detected by the X-ray detection unit in consideration of an atom number density per unit volume in each of sections included in the plurality of three-dimensional spaces and an atomic number, and reconstructs the tomographic image in consideration of the scattered ray component.

According to another embodiment of the present invention, there is provided an image reconstruction device of an X-ray CT apparatus, that performs a reconstruction of a tomographic image of an irradiation target based on image data of X-rays passed through the irradiation target, where the image reconstruction device calculates a scattered ray component scattered in each of a plurality of three-dimensional spaces obtained by partitioning the irradiation target by a predetermined size among the X-rays detected by the X-ray detection unit in consideration of an atom number density per unit volume in each of sections included in the plurality of three-dimensional spaces and an atomic number, and reconstructs the tomographic image in consideration of the scattered ray component.

According to still another embodiment of the present invention, there is provided An image reconstruction method in an X-ray CT apparatus, for reconstructing a tomographic image of an irradiation target based on image data of X-rays passed through the irradiation target, the method including: calculating a scattered ray component scattered in each of a plurality of three-dimensional spaces obtained by partitioning the irradiation target by a predetermined size among the X-rays detected by the X-ray detection unit in consideration of an atom number density per unit volume in each of sections included in the plurality of three-dimensional spaces and an atomic number; and reconstructing the tomographic image in consideration of the scattered ray component.

DETAILED DESCRIPTION

X-rays detected by the X-ray detector include direct rays that have passed through an irradiation target and scattered rays. Since scattered rays are components that can be the noise at the time of an image reconstruction, the quality of the reconstructed image may be degraded.

It is desirable to provide an X-ray CT apparatus capable of obtaining a CT image with improved image quality.

As described above, it is possible to more accurately calculate a scattered ray component in consideration of a tissue or the like inside the irradiation target by calculating a scattered ray component scattered in each of the plurality of three-dimensional spaces among the X-rays detected by the X-ray detection unit in consideration of an atom number density per unit volume in each of a plurality of three-dimensional spaces obtained by partitioning the irradiation target by a predetermined size and an atomic number, and by adopting a configuration in which an image reconstruction is performed in consideration of the calculation result. Since the image reconstruction can be performed in a state where the amount of the scattered ray component is small by adopting a configuration in which the image reconstruction is performed in consideration of the scattered ray component calculated as described above, the image quality of the CT image to be obtained can be improved.

Here, when the X-ray CT apparatus is a cone beam CT apparatus, the above operation is effectively achieved. Since the angle of view is large in the cone beam CT apparatus, the image quality is likely to be deteriorated due to the influence of the scattered ray component. Therefore, when the above configuration is applied to the cone beam CT apparatus, the effect of improving the image quality becomes higher.

According to the present invention, an X-ray CT apparatus capable of obtaining a CT image with improved image quality is provided.

Hereinafter, an embodiment for carrying out the present invention will be described in detail with reference to the accompanying drawings. In the description of the drawings, the same elements will be denoted by the same reference symbols, and the redundant description thereof will be omitted.

Figure 1:
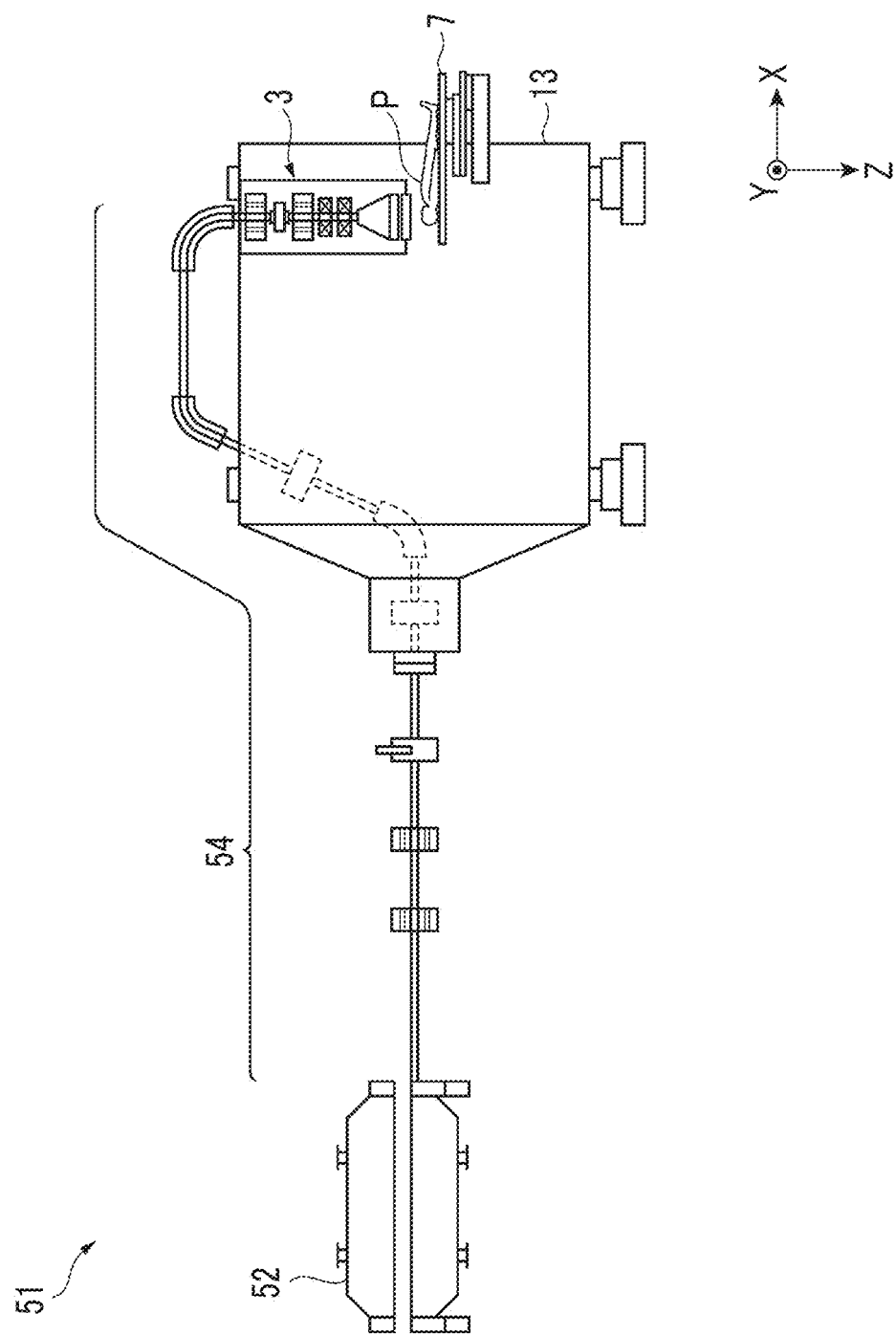
FIG. 1 is a diagram showing a charged particle beam therapy system in which an X-ray CT apparatus according to a present embodiment is incorporated.
Figure 2:
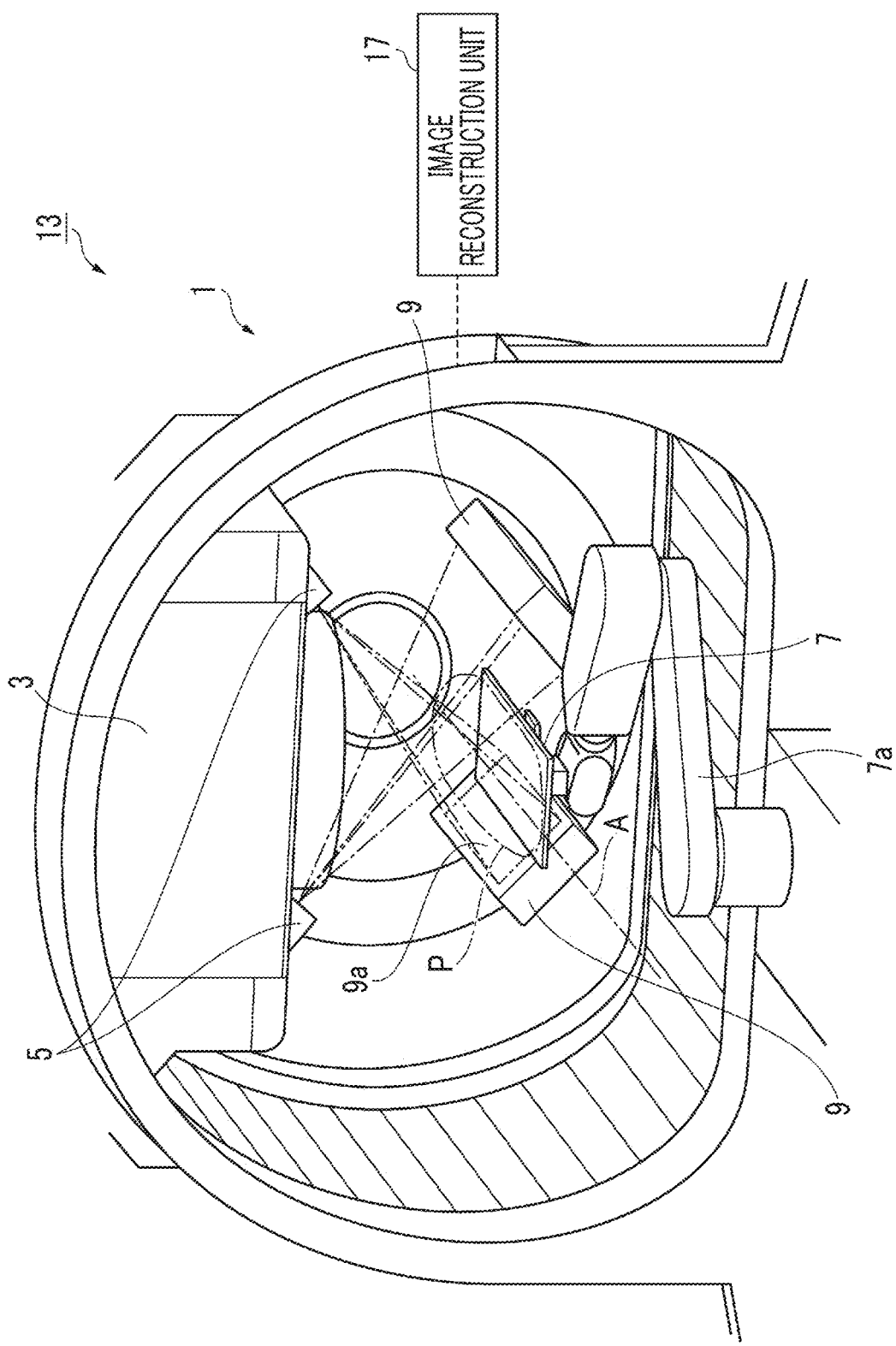
FIG. 2 is a perspective view showing a rotary gantry of the charged particle beam therapy system.

As shown in FIGS. 1 and 2, the X-ray CT apparatus 1 of the present embodiment is incorporated in a charged particle beam therapy system 51 (for example, a proton beam therapy system). The charged particle beam therapy system 51 is, for example, an apparatus that performs treatment by irradiating lesions (for example, a tumor or the like) inside a patient P (irradiation target) with a charged particle beam. The charged particle beam therapy system 51 includes an accelerator 52 that accelerates charged particles (for example, hydrogen ions) to emit a charged particle beam (proton beam), an irradiation unit (irradiation nozzle) 3 that irradiates a patient P with the charged particle beam, a rotary gantry 13 that rotates the irradiation unit 3 about a rotation axis A around a treatment table 7 on which the patient P is placed, and a transport line 54 that connects the accelerator 52 to the irradiation unit 3 and transports the charged particle beam emitted from the accelerator 52 to the irradiation unit 3.

The X-ray CT apparatus 1 is a CT apparatus called a cone beam CT (CBCT) apparatus, and is used for the purpose of accurately adjusting the position of the patient P on the treatment table 7 of the charged particle beam therapy system 51. Specifically, before a proton beam irradiation treatment is performed, a tomographic image (CT image) of the patient P in a state of being set on the treatment table 7 is created by using the X-ray CT apparatus 1, and the position of the lesion or the like of the patient P is recognized based on the CT image. The CT image obtained by the X-ray CT apparatus 1 is compared with a CT image for a treatment plan of the patient P created by another CT apparatus in advance, and the positioning of the patient P on the treatment table 7 is performed. The positioning of the patient P on the treatment table 7 may be directly performed based on the CT image obtained by the X-ray CT apparatus 1.

Figure 3:
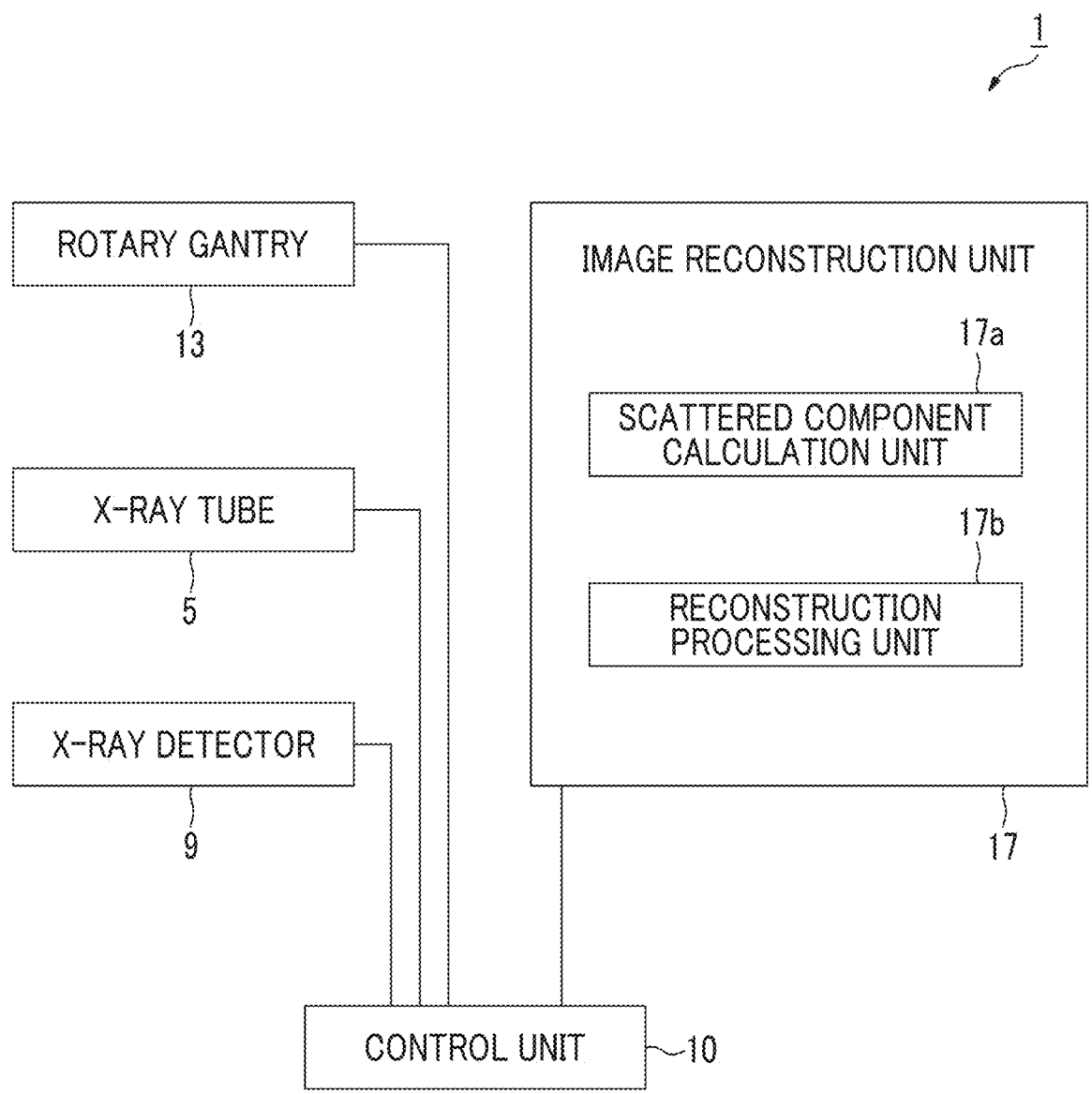
FIG. 3 is a block diagram showing functional components of the X-ray CT apparatus.

The X-ray CT apparatus 1 includes an X-ray tube 5 (X-ray irradiation unit) that irradiates the patient P with X-rays, the treatment table 7 (placement portion) on which the patient P is placed, and an X-ray detector (X-ray detection unit) 9 that detects X-rays. As shown in FIG. 2, the X-ray CT apparatus 1 of the present embodiment includes two sets of the X-ray tube 5 and the X-ray detector 9, but the number of sets of the X-ray tube 5 and the X-ray detector 9 may be one. The X-ray CT apparatus 1 includes an image reconstruction unit 17 that generates a CT image of the inside of the patient P based on the X-rays detected by the X-ray detector 9. Further, as shown in FIG. 3, the X-ray CT apparatus 1 includes the X-ray tube 5, the X-ray detector 9, the rotary gantry 13 (support portion), and a control unit 10 that controls the image reconstruction unit 17. The image reconstruction unit 17 includes a scattered component calculation unit 17a and a reconstruction processing unit 17b. The function of the image reconstruction unit 17 will be described later.

As shown in FIG. 2, the X-ray tube 5 and the X-ray detector 9 are rotatably supported by the rotary gantry 13, and the X-ray tube 5 and the X-ray detector 9 are integrally rotated around the rotation axis A. That is, the X-ray tube 5 and the X-ray detector 9 can circulate around the treatment table 7. In the present embodiment, a case where the X-ray tube 5 and the X-ray detector 9 rotate in a circular orbit about the rotation axis A will be described as an example. The X-ray tube 5 irradiates the treatment table 7 with a cone-shaped X-ray beam (cone beam) having the X-ray tube 5 as a vertex. The X-ray detector 9 is a flat panel detector (FPD) and has a large number of detection pixels 9a for detecting X-rays from the X-ray tube 5. The detection pixels 9a are two-dimensionally disposed on a plane orthogonal to an axis of the cone-shaped X-ray beam in the X-ray detector 9.

The X-ray tube 5 and the X-ray detector 9 are disposed at positions opposite to each other with the treatment table 7 interposed therebetween in the rotary gantry 13. X-rays emitted from the X-ray tube 5 and passed through the patient P on the treatment table 7 are detected by the X-ray detector 9, and X-ray image data of the patient P is acquired by the X-ray detector 9. At this time, X-ray image data corresponding to each projection angle can be collected while changing the projection angle, by rotating the rotary gantry 13 by a predetermined angle (for example, about 180°). Further, at this time, the treatment table 7 on which the patient P is placed is supported by a support device 7a fixed to a floor of a building, and the patient P is displaced near the rotation axis A regardless of the rotation of the rotary gantry 13. Then, the image reconstruction unit 17 executes image reconstruction processing according to a predetermined calculation, based on the X-ray image data collected by the X-ray detector 9 to generate the CT image of the inside of the patient P.

Next, the image reconstruction processing in which the X-ray detector 9 by the image reconstruction unit 17 of the X-ray CT apparatus 1 generates the CT image (tomographic image) of the patient P based on the X-ray image data collected will be described. Here, it is assumed that a CT image of a tomography along a plane section orthogonal to the rotation axis A is generated. The X-ray detector 9 outputs detection data indicating the intensity of X-rays detected by each detection pixel 9a to the image reconstruction unit 17 as an electric signal, and the image reconstruction unit 17 performs predetermined image reconstruction processing based on the input detection data to obtain a CT image of the patient P. For example, the image reconstruction unit 17 is configured by a computer that operates in accordance with an image reconstruction processing program prepared in advance. The scattered component calculation unit 17a and the reconstruction processing unit 17b included in the image reconstruction unit 17 are components realized by the operation of the computer as described above.

The X-rays emitted from the X-ray tube 5 and passed through the patient P enters each detection pixel 9a included in the X-ray detector 9. However, the X-rays incident on the detection pixels 9a include scattered X-rays (scattered rays) generated when the irradiated X-rays (primary X-rays: direct rays) interact within the patient P. Since the detection pixels 9a detect both the direct rays and the scattered rays, the X-ray image data includes information on the intensity of the X-rays including both the direct rays and the scattered rays. Therefore, when the image reconstruction processing is performed in the image reconstruction unit 17, there is a possibility that the image quality is deteriorated due to the influence of the scattered rays.

In contrast, in the image reconstruction unit 17 of the X-ray CT apparatus 1 according to the present embodiment, processing of specifying the scattered ray component included in the detection data indicating the intensity of X-rays (detection data) detected by each detection pixel 9a in the scattered component calculation unit 17a is performed. Then, the reconstruction processing unit 17b estimates the scattered ray component included in the detection data detected by each of the detection pixels 9a, and then performs processing of subtracting the estimated scattered ray component in the image reconstruction processing.

In order for the scattered ray component calculation unit 17a to specify the scattered ray component, it is necessary to specify the component of the X-rays incident on each detection pixel 9a.

Figure 4:
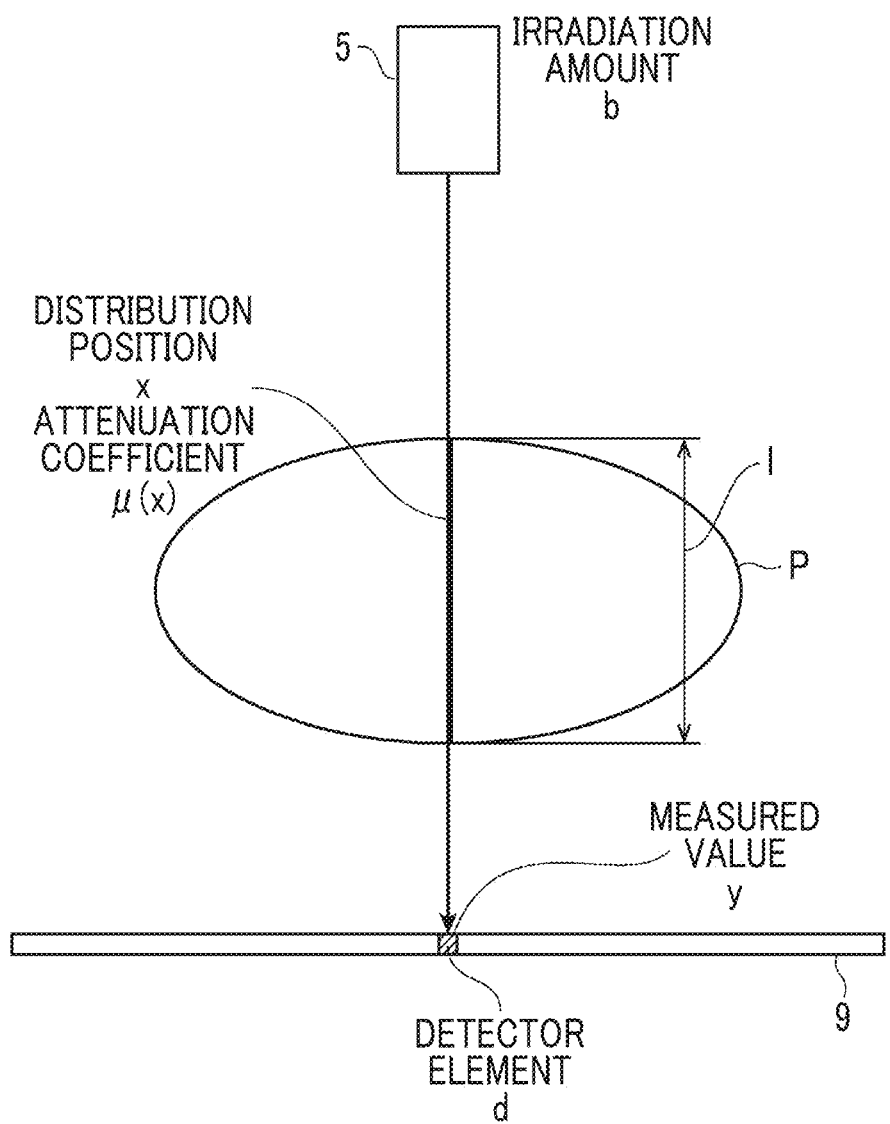
FIG. 4 is a diagram showing a technique of an image reconstruction that is performed in the related art.

First, a technique of the image reconstruction that is performed in the related art (maximum likelihood estimation-expected value maximization method: ML-EM method) will be described with reference to FIG. 4. In the image reconstruction processing, a successive approximation method is used. In the image reconstruction technique in the related art, an objective function (likelihood function) is set and a parameter x that maximizes the function is obtained. As shown in FIG. 3, it is assumed that X-rays emitted from the X-ray tube 5 pass through the patient P and enter a detector element d corresponding to a specific detection pixel 9a included in the X-ray detector 9. Here, assuming that the intensity of the X-rays detected by the detector element d is y, an objective function P(y) can be represented as the following Equation (1). Note that, x represents a specific position of the patient P on an optical path of the X-rays (direct rays) incident on the detector element d. Further, λ(x) is an expected value of the intensity y of X-rays detected by the detector element d, and can be represented as a function of x.

[Equation 1]

$$P(y) = \frac{\lambda(x)^y}{y!} \exp[-\lambda(x)] \quad (1)$$

At this time, when x that maximizes P(y) is specified, P(y) satisfies the following Equation (2).

[Equation 2]

$$\frac{\partial}{\partial x} P(y) = 0 \quad (2)$$

In addition, the expected value λ(x) can be represented by the following Equation (3), when an amount of X-rays emitted from the X-ray tube 5 is b, a transmission length of X-rays is l, and an attenuation coefficient of X-rays at the position x is μ(x).

[Equation 3]

$$\lambda(x) = b \exp[-l \cdot \mu(x)] \quad (3)$$

In the method in the related art, the processing is performed in which the attenuation coefficient μ(x) at the position x is obtained based on the above equation, and the tissue or the like of each part of the patient P is specified from the attenuation coefficient.

However, X-rays actually detected by the detector element d include not only direct rays but also scattered rays. That is, the actual measured value y should be the sum of the direct rays and the scattered rays. That is, the expected value λ(x) should be indicated as the sum of the expected values of the direct rays and the scattered rays, while being the expected value λ(x) related to the direct rays described above. Therefore, the Convex method in which the objective function of the above technique (maximum likelihood estimation-expected value maximization method: ML-EM method) is convexly transformed and the Newton method is applied is used.

Figure 5:
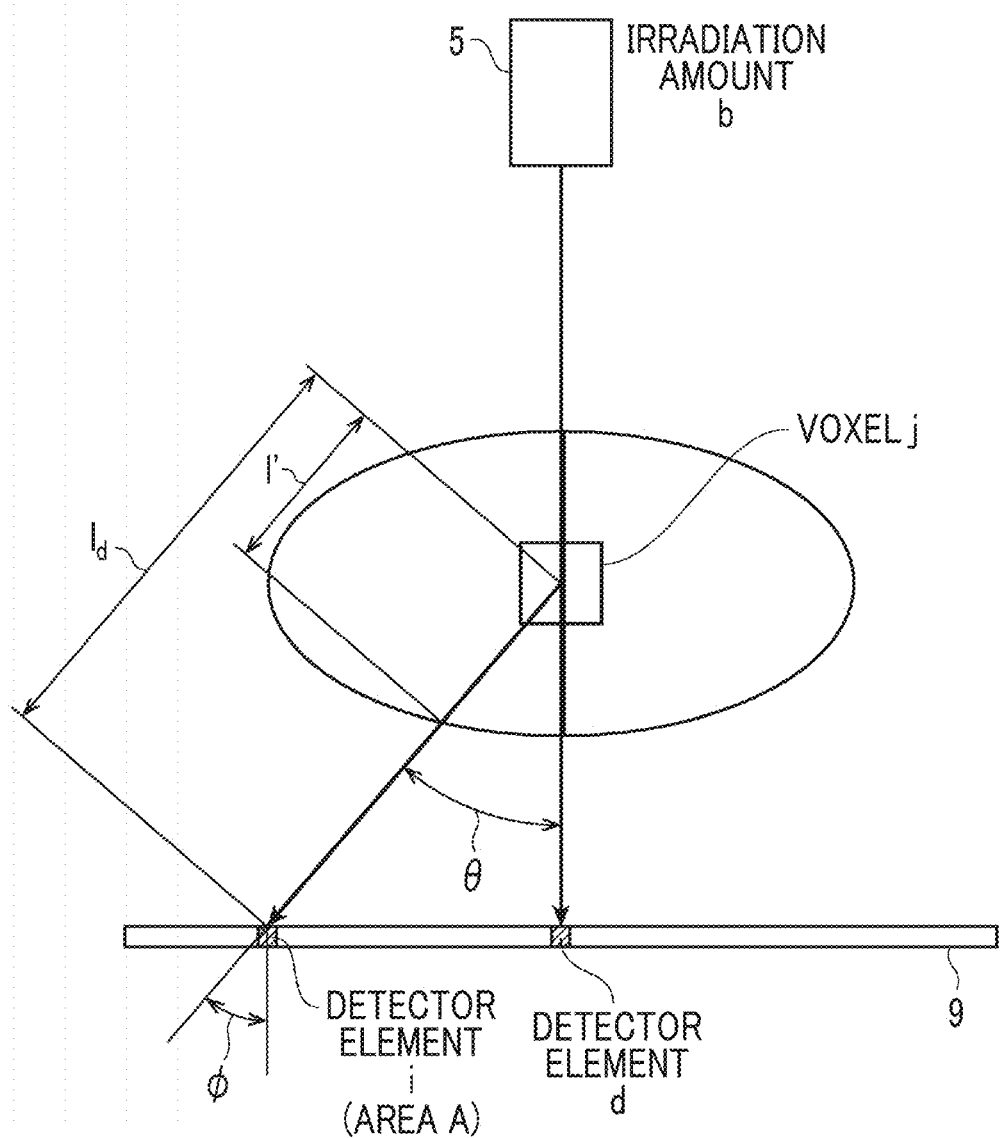
FIG. 5 is a diagram showing a technique of calculating a scattered ray component.

The expected value of the scattered rays will be described with reference to FIG. 5. Here, the attention is paid to a voxel j, which is one section of a specific three-dimensional space in the patient P. Then, it is assumed that the X-rays emitted from the X-ray tube 5 are scattered at the specific voxel j, and enter a detector element i (which is a detector element different from the detector element d) corresponding to the specific detection pixel 9a included in the X-ray detector 9.

The expected value $s_{ie-dj}$ of the X-rays scattered at the voxel j and incident on the detector element i can be represented as the following Equation (4). The expected value $S_{ie-dj}$ indicates a value of the energy e detected by the detector element i when the X-rays incident on detector element d via the voxel j are scattered at the voxel j and incident on the detector element i.

[Equation 4]

$$s_{iedj} = \frac{d\sigma_c}{d\Omega} \cdot \frac{A\cos\phi}{L_{ij}^2} \cdot N_j \cdot Z_j \cdot \frac{1-\exp(-l_{ij}\cdot\mu_j(e'))}{\mu_j(e')} \cdot b_d \quad (4)$$

$$\exp\left(-\sum_{k<j} l_{dk} \cdot \mu_k(e')\right) \cdot \exp\left(-\sum_q l'_{iq} \cdot \mu_q(e)\right)$$

In addition, each element included in Equation (4) is as follows.

$d\sigma_c/d\Omega$ is a differential scattering cross-sectional area. $\sigma_c$ indicates a total scattering cross-sectional area. It can be specified based on the Klein Nishina's formula for obtaining the scattering cross-sectional area of light scattering.

A cos $\phi/L_{ij}^2$ is a solid angle of the detector element i. A is an area of the light receiving surface of the detector element i, φ is an angle between the incident X-rays and a normal line of the detector element i and is the same as a scattering angle θ, and $L_{ij}$ is a distance from the voxel j to the detector element i.

$N_j$ is an atom number density per unit volume when the voxel j is assumed to be composed of a single substance.

$Z_j$ is an atomic number when the voxel j is assumed to be composed of a single substance.

1−exp $(-l_{ij}\cdot\mu_j(e'))$ is a probability that X-rays react with the patient P in the voxel j. $l_{ij}$ is a transmission length of X-rays incident on the detector element i with respect to the voxel j, and e is an energy index of the X-rays. An index is given to each X-ray having the energy of a predetermined range.

$\mu_j(e')$ is an attenuation coefficient of X-rays having the energy e' at the voxel j.

$b_d \exp(-\Sigma l_d \cdot \mu(e'))$ is a probability that X-rays transmit from the X-ray tube 5 to the voxel j. $\Sigma l_d$ is the distance from the voxel j to the detector.

$\exp(-\Sigma l'_i \cdot \mu(e))$ is the probability that X-rays transmit from the voxel j to the detector element i. $l'_i$ is a transmission length from the voxel j to the detector element i.

Equation (4) represents a scattered ray component when focusing on voxel j. However, in practice, the scattered rays are also generated in other voxels and are incident on the detector element i. Therefore, the scattered ray component detected by the detector element i can be represented as the following Equation (5) based on Equation (4).

[Equation 5]

$$s_{ie} = \sum_{d \neq i,j} s_{iedj} \quad (5)$$

In a case where the scattered ray component represented by the above Equation (5) can be specified, an expected value of the scattered ray component detected by the detector element i can be obtained. However, as shown in Equation (4), the scattered ray component includes an atom number density $N_j$ per unit volume assuming that the voxel j is composed of a single substance, and an atomic number $Z_j$ assuming that the voxel j is composed of a single substance. Since they are values that change depending on the disposition of the tissue or lesion in the body of the patient P, they can take different values depending on the voxels.

On the other hand, the atom number density $N_j$ per unit volume in the voxel j and the atomic number $Z_j$ also appear in the calculation of the direct rays. As shown in Equation (6), the attenuation coefficient μ can be represented as the sum of a photoelectric absorption coefficient μphot by the photoelectric effect, an attenuation coefficient μcompt by the Compton scattering, and an attenuation coefficient μpair by the pair generation.

$$\mu = \mu_{phot} + \mu_{compt} + \mu_{pair} \quad (6)$$

Since the μpair can be ignored, μ can be represented as the sum of the μphot and μcompt. The μphot and μcompt can be represented as Equations (7) and (8) below, respectively.

[Equation 6]

$$\mu_{phot} = \frac{5}{4} N \varphi_0 \frac{Z^5}{137^4} 4\sqrt{2} \left(\frac{m_e c^2}{h\nu}\right)^{\frac{7}{2}} \quad (7)$$

$$\mu_{compt} = NZ\sigma_c \quad (8)$$

φ0 is the total cross-sectional area of Thomson scattering, me is the electron mass, c is the velocity of light, h is Planck's constant, and ν is the frequency of the incident photon.

As shown in Equations (7) and (8), the μphot and μcompt are the functions including N and Z, respectively. That is, it can be said that μ represented by the sum of them is also a function including N and Z. Therefore, when the energy is determined, μ can be obtained as in Equations (9) to (11) by using N and Z.

[Equation 7]

$$\mu = \mu_{phot} + \mu_{compt} + \mu_{pair} = N_j Z_j^5 f_{phot}(E) + N_j Z_j f_{compt}(E) \quad (9)$$

$$f_{phot}(E) = \frac{5\varphi_0}{137^4}\sqrt{2}\left(\frac{m_e c^2}{h\nu}\right)^{\frac{7}{2}} \quad (10)$$

$$f_{compt}(E) = \varphi_0 \frac{3}{4}\left\{\frac{1+\gamma}{\gamma^3}\left[\frac{2\gamma(1+\gamma)}{1+2\gamma} - \log(1+2\gamma)\right] + \frac{1}{2\gamma}\log(1+2\gamma) - \frac{1+3\gamma}{(1+2\gamma)^2}\right\} \quad (11)$$

Here, in a case of an objective function Q of the entire system, Q can be represented as the following Equation (12).

[Equation 8]

$$Q(\mu | \mu^*) = -\sum_{ie}\sum_j \frac{l_{ij} \cdot \mu_j^n(e)}{\sum_j l_{ij} \cdot \mu_j^n(e)}\left[(y_{ie} - s_{ie})\left(\ln b_{ie} - \frac{\mu_j(e)}{\mu_j^n(e)}\sum_j l_{ij} \cdot \mu_j^n(e)\right) - \ln\right.$$

$$\left. (y_{ie} - s_{ie}) - b_{ie}\exp\left[-\frac{\mu_j(e)}{\mu_j^n(e)}\sum_j l_{ij} \cdot \mu_j^n(e)\right]\right] \quad (12)$$

Since the objective function Q includes μ(x), it can be represented as a function of N and Z using the above equation. By making use of this and creating a successive approximation formula using the Newton method, N and Z can be represented as the following Equations (13) and (14).

[Equation 9]

$$N_j^{n+1} = N_j^n - \frac{\partial Q}{\partial N_j} \bigg/ \frac{\partial^2 Q}{\partial N_j^2} =$$

$$N_j^n + \frac{N_j^n \sum_{ie} l_{ij}(Z_j^{n4} f_{phot}(e) + f_{compt}(e)) \cdot \left[b_{ie}\exp\left(-\sum_j l_{ij} \cdot \mu_j^n(e)\right) - (y_{ie} - s_{ie})\right]}{\sum_{ie} l_{ij}(Z_j^{n4} f_{phot}(e) + f_{compt}(e)) \cdot \left(\sum_j l_{ij} \cdot \mu_j^n(e)\right) \cdot b_{ie}\exp\left(-\sum_j l_{ij} \cdot \mu_j^n(e)\right)} \quad (13)$$

$$Z_j^{n+1} = Z_j^n - \frac{\partial Q}{\partial Z_j} \bigg/ \frac{\partial^2 Q}{\partial Z_j^2} =$$

$$Z_j^n + \frac{\left(Z_j^n \sum_{ie} l_{ij}(5Z_j^{n4} f_{phot}(e) + f_{compt}(e)) \cdot \left[b_{ie}\exp\left(-\sum_j l_{ij} \cdot \mu_j^n(e)\right) - (y_{ie} - s_{ie})\right]\right)}{\left(\sum_{ie} l_{ij}\left[\frac{(5Z_j^{n4} f_{phot}(e) + f_{compt}(e))^2}{Z_j^{n4} f_{phot}(e) + f_{compt}(e)} \cdot \left(\sum_j l_{ij} \cdot \mu_j^n(e)\right) \cdot b_{ie}\exp\left(-\sum_j l_{ij} \cdot \mu_j^n(e)\right) - 20Z_j^{n4} f_{phot}(e)\left[b_{ie}\exp\left(-\sum_j l_{ij} \cdot \mu_j^n(e)\right) - (y_{ie} - s_{ie})\right]\right]\right)} \quad (14)$$

Note that, $f_{phot}$ and $f_{compt}$ correspond to the above-described equations (10) and (11).

By using the above Equations (13) and (14), $N_j$ and $Z_j$ in the voxel j can be calculated. Then, by using these Nj and Zj, the scattered ray component can be calculated from the voxel j based on Equation (4). By calculating N and Z in each voxel, the scattered ray component from each voxel can be calculated. That is, the scattered ray component detected by the detector element i can be calculated based on Equation (5).

The scattered ray component of the X-rays detected by each detection pixel 9a (the above-described detector element) can be calculated by performing the series of calculations described-above, and thus is possible to calculate an accurate physical property value excluding the influence by the scattered rays from the detection value of each detection pixel 9a.

Figure 6:
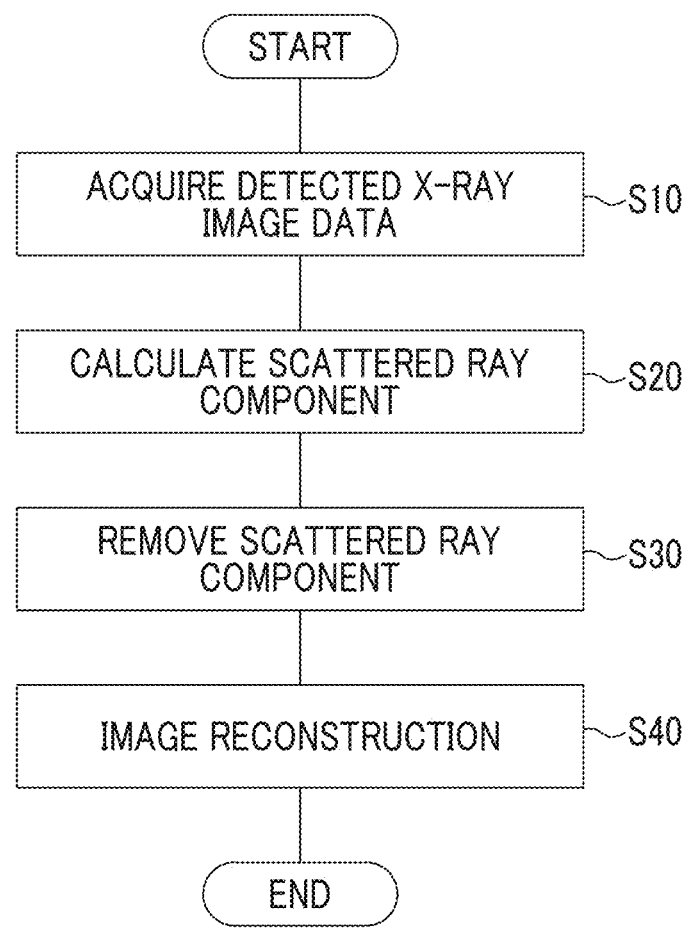
FIG. 6 is a flowchart showing control processing when an image reconstruction unit reconstructs an image of an irradiation target.

Next, control processing when the image reconstruction unit 17 reconstructs the image of the irradiation target 30 will be described with reference to the flowchart in FIG. 6.

First, the image reconstruction unit 17 acquires X-ray image data at each projection angle from the X-ray detector 9 (step S10). Next, the image reconstruction unit 17 estimates N and Z of each voxel from the acquired X-ray image data. The scattered component calculation unit 17a calculates the scattered ray component for each projection angle and for each detection pixel based on the estimated N and Z (step S20). As a method of calculating the scattered ray component, for example, the method described above can be used. Note that, since the calculation of the scattered component requires an image after the image reconstruction, the calculation is performed every single time the image reconstruction processing is repeated. Next, the reconstruction processing unit 17b removes a scattered ray component from the X-ray image data acquired by the X-ray detector 9 (step S30). The processing in S20 and S30 described-above is performed for each of a plurality of detection pixels included in the image data for each of the plurality of X-ray image data obtained by capturing images at each projection angle. Then, the reconstruction processing unit 17b performs the image reconstruction by using the X-ray image data from which the scattered ray component has been removed (step S40). As described above, the reconstructed image is completed, and the processing shown in FIG. 6 ends.

Next, the operations and effects of the X-ray CT apparatus 1 according to the present embodiment will be described.

As described above, the X-ray CT apparatus 1 calculates the scattered ray component scattered in each of the plurality of three-dimensional spaces among the X-rays detected by the X-ray detector 9 (X-ray detection unit) considering the atom number density N per unit volume in each of the sections (corresponds to the voxel in the embodiment described-above) included in the plurality of three-dimensional spaces obtained by partitioning the patient P as the irradiation target by a predetermined size and the atomic number Z, and performs the image reconstruction in consideration of the calculation result. With such a configuration, it is possible to more accurately calculate the scattered ray component in consideration of a tissue or the like inside the irradiation target.

In the treatment of a patient using the charged particle beam therapy system, in order to cope with the movement and deformation of the lesion inside the patient P (irradiation target) during the treatment period, the position of the lesion inside the patient P is specified by using the X-ray CT apparatus or the like, and the treatment plan is adjusted. As a method of measuring the inside of the patient P for adjusting the treatment plan, the use of the X-ray CT apparatus mounted on the charged particle beam therapy system has been studied. However, the existing method of using the X-ray CT apparatus mounted on the charged particle beam therapy system in the related art is used for positioning the patient during the irradiation of the charged particle beam, and therefore there was no need for the image quality that could be used to adjust treatment plans.

On the other hand, in the X-ray CT apparatus according to the present embodiment, an accurate calculation of the scattered ray component is realized by focusing on the fact that the scattered ray component included in the X-rays detected by the X-ray detector of the X-ray CT apparatus greatly affects the deterioration of the image quality. In particular, since a configuration is adopted in which the scattered ray component is calculated in consideration of the atom number density N per unit volume in each of a plurality of three-dimensional spaces obtained by partitioning the patient P by a predetermined size and the atomic number Z, it is possible to calculate the scattered ray component in consideration of the internal tissue of the patient P including a lesion or the like. Therefore, it is possible to calculate the scattered ray component with higher accuracy than in the method of reducing the scattered ray component which has been studied so far, and to perform the image reconstruction in consideration of the result. As a result, it is possible to reduce the influence of the scattered ray component, and the quality of the reconstructed image can be improved.

Further, when the X-ray CT apparatus 1 is a cone beam CT apparatus, the above operation is effectively achieved. Because the FPD is used as the X-ray detector in the cone beam CT apparatus, the cone beam CT apparatus has a feature that the scattered ray component incident on the X-ray detector increases. Therefore, the CT image captured and reconstructed by the cone beam CT apparatus is likely to be deteriorated in image quality due to the influence of the scattered ray component. In other words, the image quality is remarkably improved by performing the image reconstruction in consideration of the scattered ray component.

The present invention is not limited to the above embodiment.

For example, in the above-described embodiment, a case where the X-ray CT apparatus 1 incorporated in the proton beam therapy system has been described as an example of the charged particle beam therapy system 51. However, it is not limited to the proton beam therapy system. For example, the X-ray CT apparatus 1 according to the present embodiment can be applied to a therapy system using a charged particle beam such as a heavy particle (heavy ion) beam, a pion beam, or the like. Further, the X-ray CT apparatus 1 is not limited to a configuration in which X-ray CT apparatus 1 is attached to a radiation therapy system such as charged particle beam therapy system 51, and a configuration in which the X-ray CT apparatus 1 is provided as a single X-ray CT apparatus may be adopted.

Further, in the above-described embodiment, a case where the X-ray CT apparatus 1 is a cone beam CT apparatus has been described, but the present invention is not limited to the cone beam CT apparatus. In addition, the configuration of each unit included in the X-ray CT apparatus can be appropriately changed according to the specifications thereof.

In the above-described embodiment, the N and Z are specified and the scattered ray component is calculated by using a method of creating a successive approximation formula by using Newton's method after describing the above objective function as a function of N and Z. However, the method of calculating the scattered ray component is not limited to the above method. Also, after calculating the scattered ray component, as the processing when performing the image reconstruction in consideration of the scattered ray component, a method different from a method of simply removing the scattered ray component (an example of preventing the scattered ray component from affecting the image quality by adding some statistical processing) maybe used. Further, the three-dimensional spaces for which N and Z are calculated is not limited to voxels. For example, a larger three-dimensional space obtained by combining a plurality of voxels may be defined.

It should be understood that the invention is not limited to the above-described embodiment, but may be modified into various forms on the basis of the spirit of the invention. Additionally, the modifications are included in the scope of the invention.

What is claimed is:

1. An X-ray CT apparatus comprising:
an X-ray irradiation unit that rotates around a placement portion on which an irradiation target is placed and emits X-rays; an X-ray detection unit that detects the X-rays emitted from the X-ray irradiation unit and passed through the irradiation target; and
an image reconstruction unit that reconstructs a tomographic image of the irradiation target based on image data of the X-rays detected by the X-ray detection unit,
wherein the image reconstruction unit calculates a scattered ray component scattered in each of a plurality of three-dimensional spaces obtained by partitioning the irradiation target by a predetermined size among the X-rays detected by the X-ray detection unit in consideration of an atom number density per unit volume in each of sections included in the plurality of three-dimensional spaces and an atomic number, and reconstructs the tomographic image in consideration of the scattered ray component.

2. The X-ray CT apparatus according to claim 1,
wherein the X-ray irradiation unit and the X-ray detection unit are disposed at positions opposite to each other with the placement portion, on which the irradiation target is placed, interposed therebetween.

3. The X-ray CT apparatus according to claim 2,
wherein the X-ray CT apparatus includes a set or a plurality of sets of the X-ray irradiation unit and the X-ray detection unit.

4. The X-ray CT apparatus according to claim 1,
wherein the image reconstruction unit includes a scattered component calculation unit and a reconstruction processing unit,
the scattered component calculation unit performs processing of specifying a scattered ray component included in the detected X-ray image data, and
the reconstruction processing unit estimates the scattered ray component included in the X-ray image data, and then performs processing of subtracting the scattered ray component from the X-ray image data.

5. The X-ray CT apparatus according to claim 4,
wherein the scattered component calculation unit calculates the scattered ray component by using a Convex method in which an objective function is convexly transformed and a Newton method is applied.

6. The X-ray CT apparatus according to claim 4,
wherein the X-ray detection unit has a plurality of detection pixels for detecting X-rays, and
the scattered component calculation unit calculates the scattered ray component of X-rays detected by each detection pixel for each projection angle and for each detection pixel.

7. The X-ray CT apparatus according to claim 6,
wherein the calculation of the scattered ray component is performed every time image reconstruction processing is repeated.

8. The X-ray CT apparatus according to claim 6,
wherein, in the scattered component calculation unit and the reconstruction processing unit, the calculation and removal of the scattered ray component are performed for each of a plurality of detection pixels included in X-ray image data, for each of a plurality of the X-ray image data captured images at each projection angle.

9. The X-ray CT apparatus according to claim 1,
wherein the X-ray CT apparatus is a cone beam CT apparatus.

10. An image reconstruction device of an X-ray CT apparatus, for reconstructing a tomographic image of an irradiation target based on X-ray image data of X-rays passed through the irradiation target,
wherein the image reconstruction device calculates a scattered ray component scattered in each of a plurality of three-dimensional spaces obtained by partitioning the irradiation target by a predetermined size among the X-rays detected by the X-ray detection unit in consideration of an atom number density per unit volume in each of sections included in the plurality of three-dimensional spaces and an atomic number, and reconstructs the tomographic image in consideration of the scattered ray component.

11. An image reconstruction method in an X-ray CT apparatus, for reconstructing a tomographic image of an irradiation target based on X-ray image data of X-rays passed through the irradiation target, the method comprising:
calculating a scattered ray component scattered in each of a plurality of three-dimensional spaces obtained by partitioning the irradiation target by a predetermined size among the X-rays detected by the X-ray detection unit in consideration of an atom number density per unit volume in each of sections included in the plurality of three-dimensional spaces and an atomic number; and
reconstructing the tomographic image in consideration of the scattered ray component.

* * * * *